United States Patent
Lee et al.

(10) Patent No.: US 7,521,565 B2
(45) Date of Patent: Apr. 21, 2009

(54) PROCESS FOR PREPARING 1,2,3,9-TETRAHYDRO-9-METHYL-3-[(2-METHYL-1H-IMIDAZOLE-1-YL)METHYL]-4H-CARBAZOL-4-ONE OR ITS SALT

(75) Inventors: Tai Au Lee, Seoul (KR); Sang Sun Park, Suwon-si (KR); Doo Byung Lee, Anyang-si (KR); Sang Jung Kim, Cheongju-si (KR)

(73) Assignee: Yuhan Corporation (KR)

( * ) Notice: Subject to any disclaimer, the term of this patent is extended or adjusted under 35 U.S.C. 154(b) by 249 days.

(21) Appl. No.: 10/574,795

(22) PCT Filed: Oct. 15, 2004

(86) PCT No.: PCT/KR2004/002646

§ 371 (c)(1),
(2), (4) Date: Apr. 3, 2006

(87) PCT Pub. No.: WO2005/037822

PCT Pub. Date: Apr. 28, 2005

(65) Prior Publication Data

US 2007/0129414 A1    Jun. 7, 2007

(30) Foreign Application Priority Data

Oct. 16, 2003    (KR) .................... 10-2003-0072096

(51) Int. Cl.
*C07D 403/06*    (2006.01)
(52) U.S. Cl. .................................................. 548/311.4
(58) Field of Classification Search ............... 548/311.4
See application file for complete search history.

(56) References Cited

U.S. PATENT DOCUMENTS 6,388,091 B1 *   5/2002   Lee et al. ................. 548/311.4

* cited by examiner

*Primary Examiner*—Laura L. Stockton
(74) *Attorney, Agent, or Firm*—Baker Hostetler, LLP

(57) ABSTRACT

1,2,3,9-tetrahydro-9-methyl-3-[(2-methyl-1H-imidazol-1-yl)methyl]-4H-carbazol-4-one or its salt is prepared in high yield by reacting a compound of formula 2 with a compound of formula 3 and a compound of formula 4 in the presence of an acid, an alkylsilylhalide compound or an acylhalide compound, in a solvent, and thus, such an inventive process can be favorably applied to a large-scale mass production thereof.

10 Claims, No Drawings

PROCESS FOR PREPARING 1,2,3,9-TETRAHYDRO-9-METHYL-3-[(2-METHYL-1H-IMIDAZOLE-1-YL)METHYL]-4H-CARBAZOL-4-ONE OR ITS SALT

FIELD OF THE INVENTION

The present invention relates to a process for preparing 1,2,3,9-tetrahydro-9-methyl-3-[(2-methyl-1H-imidazole-1-yl)methyl]-4H-carbazol-4-one or its salt, which is used as an anti-vomiting agent.

BACKGROUND OF THE INVENTION 1,2,3,9-tetrahydro-9-methyl-3-[(2-methyl-1H-imidazole-1-yl)methyl]-4H-carbazol-4-one or its salt is a useful compound as an anti-vomiting agent due to its selective action on 5-$HT_3$ receptor, which is represented by the following chemical structure:

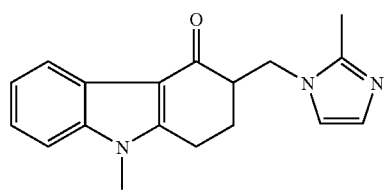

1

The compound of formula 1 may be prepared by various methods, for example, as disclosed in GB Pat. No. 2,153,821, EP Pat. No. 219,929, EP Pat. No. 221,629, KR Pat. No. 0217466, KR Pat. No. 0216422, KR Pat. No. 0377578, and KR Pat. Pub. No. 2002-0039223 (corresponding to EP Pub. No. 1207160).

The process disclosed in GB Pat. No. 2,153,821 may be summarized as following reaction scheme 1:

so long time for carrying out the reactions of each step, and the yield of final product is very low.

The process disclosed in EP Pat. No. 219,929 may be summarized as following reaction scheme 2:

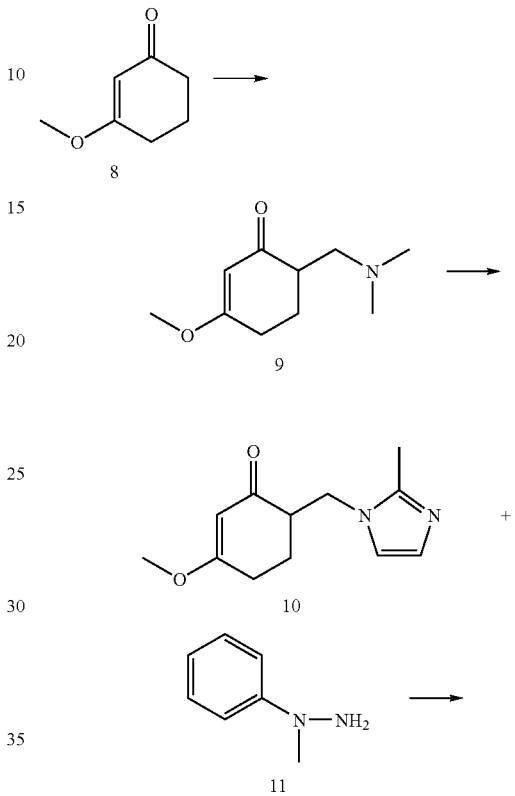

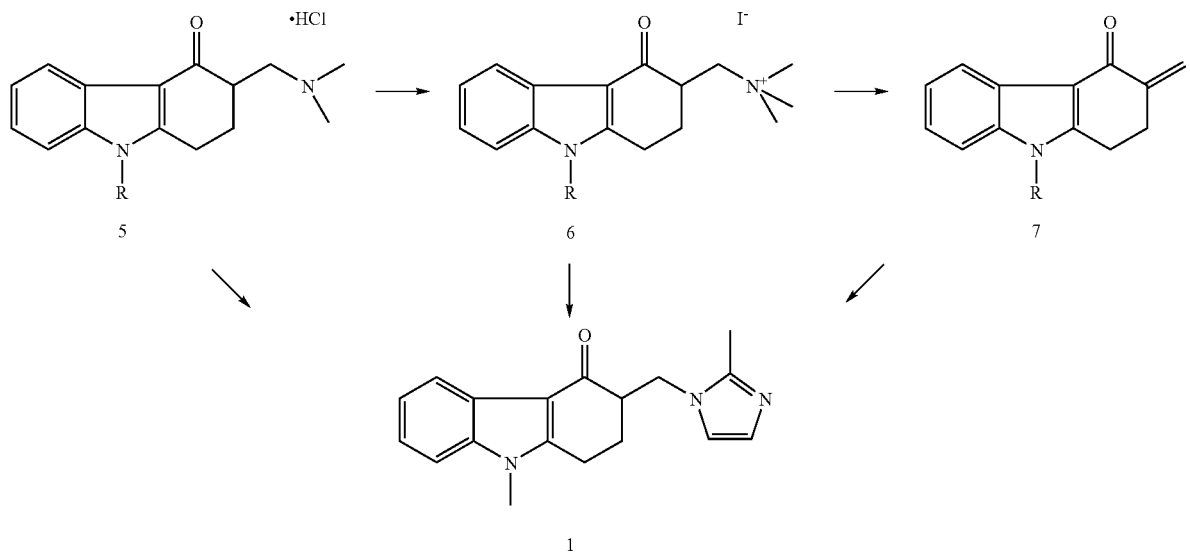

However, the above processes have the problems that the processes are completed through so many steps, which take -continued

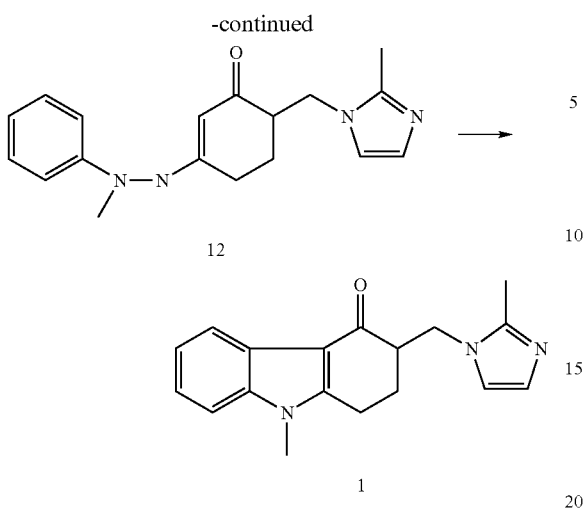

12

1

In the above reaction, an anhydrous condition is required in order to introduce a dimethylamino group. Further, the process is completed through so many steps and employs an expensive agent. Accordingly, the process disclosed in EP Pat. No. 219,929 has difficulties to be applied to an industrial-scale mass production.

The process disclosed in EP Pat. No. 221,629 may be summarized as following reaction scheme 3:

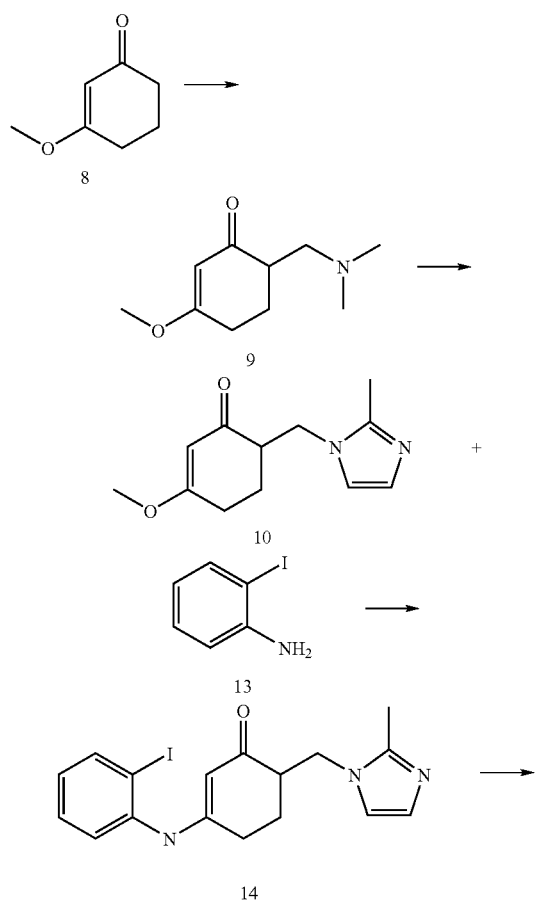

-continued

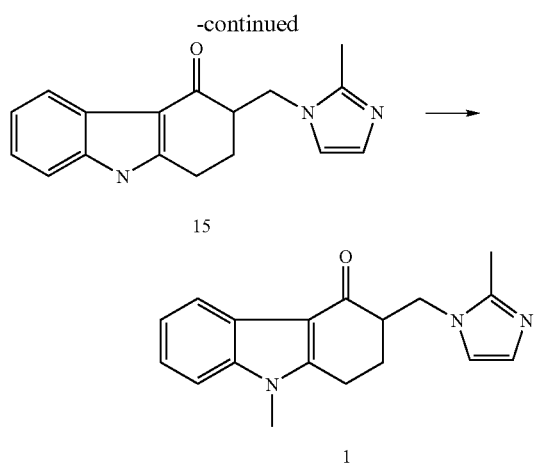

15

1

However, the above process also has difficulties to be applied to an industrial-scale mass production in that the yield of final product is very low and the process employs very expensive catalyst.

The process disclosed in KR Pat. No. 0217466 may be summarized as following reaction scheme 4:

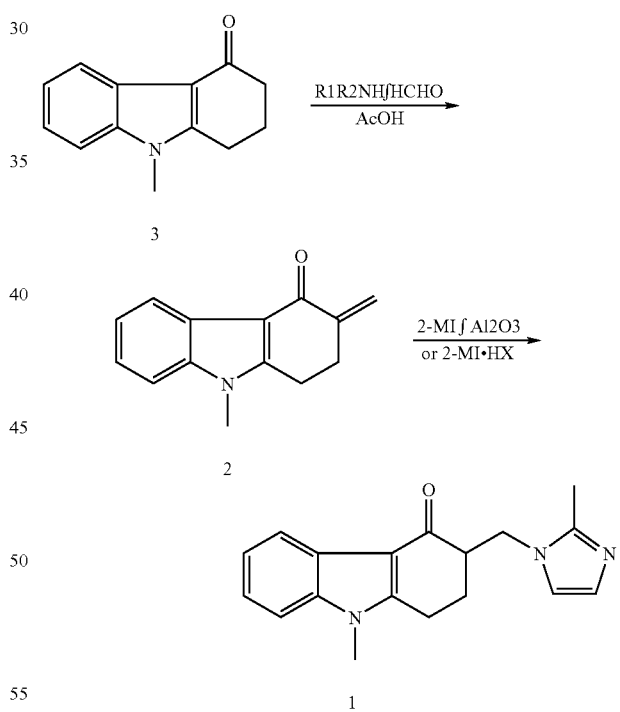

However, the above process has the problems that the process employs excess acetic acid in order to prepare the compound of formula 2, which makes it difficult to carry out a work-up process after completion of reaction, and an additional isolation process is necessary in order to remove impurities.

KR Pat. No. 0217466 discloses a process for preparing the compound of formula 1, which comprises reacting the compound of formula 2 with an acid salt of 2-methyl imidazole.

However, the reaction described in KR Pat. No. 0217466 is carried out at a high temperature, i.e. above 130° C., which is unfavorable for industrial-scale mass production.

The process disclosed in KR Pat. No. 0377578 and KR Pat. Pub. No. 2002-0039223 (corresponding EP 1207160 A1) may be summarized as following reaction scheme 5:

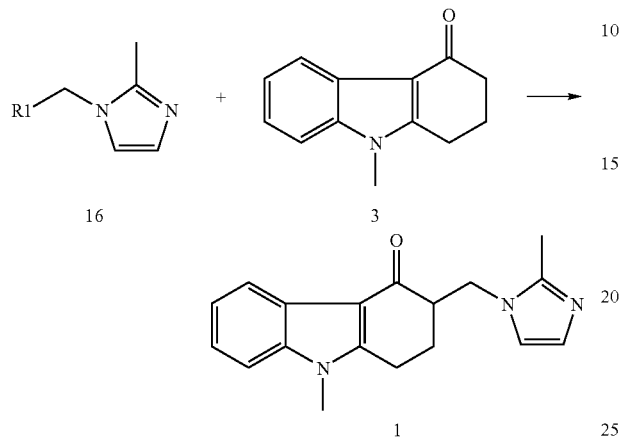

The above process has the problem that the process requires an additional reaction step in order to prepare the starting material of formula 16, which have to be isolated by high vacuum distillation. Accordingly, the above process has difficulties to be applied to an industrial-scale mass production.

DISCLOSURE OF THE INVENTION

The present invention provides an improved process for preparing 1,2,3,9-tetrahydro-9-methyl-3-[(2-methyl-1H-imidazole-1-yl)methyl]-4H-carbazol-4-one or its salt in high purity and in high yield by one-step reaction, so as to be favorably applied to a large-scale mass production thereof.

In one aspect of the present invention, there is provided a process for preparing a compound of formula 1, which comprises: reacting a compound of formula 2 with a compound of formula 3 and a compound of formula 4 in the presence of an acid, an alkylsilylhalide compound or an acylhalide compound, in a solvent:

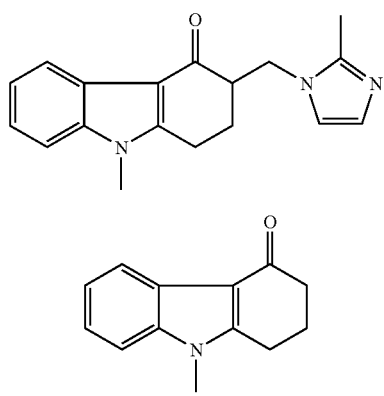

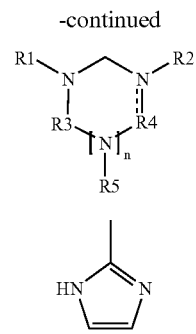

wherein, n is 0 or 1, and if n is 0, $R^1$, $R^2$, $R^3$ and $R^4$ are each independently $C_{1-6}$ alkyl group, phenyl group, —$(CH_2)_m$— ring compound or —$(CH_2)_a$—X—$(CH_2)_b$— ring compound, wherein m, a and b are each independently 1 to 5; X is N, O or S, or if n is 1, $R^1$, $R^2$ and $R^5$ are each independently $C_{1-6}$ alkyl group or aryl group; $R^3$ and $R^4$ are each independently —$CH_2$— group.

The above and other features and advantages of the present invention will become more apparent by describing in detail a preferred embodiment thereof.

BEST MODE FOR CARRYING OUT THE INVENTION

In the present invention, a compound of formula 1 or its salt is prepared in high purity and yield by one-step reaction, i.e., by reacting a compound of formula 2 with a compound of formula 3 and a compound of formula 4 in the presence of an acid, an alkylsilylhalide compound or an acylhalide compound, in n solvent, as shown in the following reaction scheme 6:

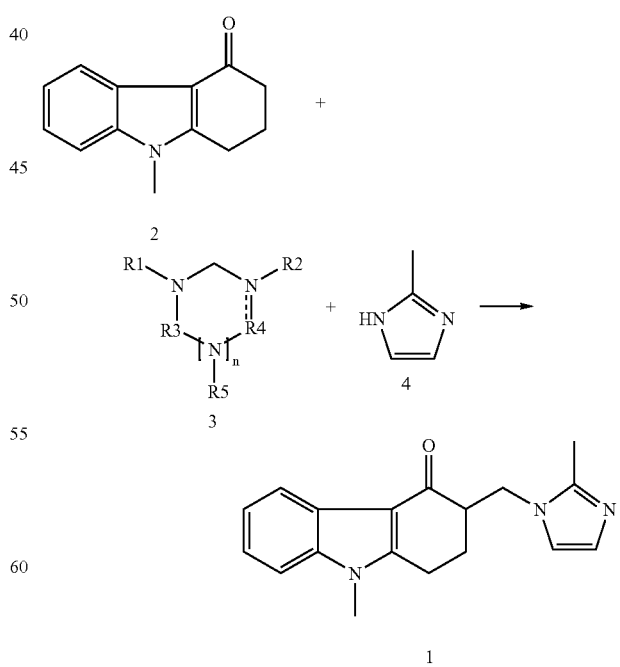

wherein, n, $R^1$, $R^2$, $R^3$, $R^4$ and $R^4$ have the same meanings as defined above.

The compounds of formula 2 and formula 3, which are starting material in the process of the present invention, may be prepared by a method which is known in the art (*J. Org. Chem.*, 1980, 45, 2938; *Synthesis*, 1990, 215; *Tetrahedron*, 1997, 53, 2941; *J. Chem. Soc, Perkin Trans, I.*, 1989, 2117; *Org. Syn.*, coll VI, 474; and *J. Org. Chem.*, 2000, 65, 8384), and it is commercially available. The compound of formula 4 is also commercially available.

For example, the compound of formula 3 may include (if n=0) N,N,N',N'-tetramethyldiaminomethane, N,N,N',N'-tetraethyldiaminomethane, N,N,N',N'-tetrabutyldiaminomethane, dipiperidinomethane, 1,1'-methylenebis(3-methylpiperidine) and 4,4'-methylenedimorphorine; and (if n=1) 1,3,5-tribenzylhexahydro-1,3,5-triazine, 1,3,5-triethylhexahydro-1,3,5-triazine and 1,3,5-trimethylhexahydro-1,3, 5-triazine.

The amount of the compound of formula 3 is preferably in the range of about 0.3~10 eq., more preferably 1~5 eq. based on the amount of the compound of formula 2., and the amount of the compound of formula 4 is preferably in the range of about 1~10 eq., more preferably 1~5 eq. based on the amount of the compound of formula 2.

The acid may be selected from the group consisting of an organic acid, representative examples thereof including hydrochloric acid, sulfuric acid, acetic acid, trifluoroacetic acid and methanesulfonic acid, and Lewis acid, representative examples thereof including aluminum chloride, zinc chloride, iron chloride(III), iron chloride(II), tin chloride and boron trifluoride.

The alkylsilylhalide compound may be selected from the group consisting of chlorotrimethylsilane, trichloromethylsilane and t-butyldimethylsilyl chloride.

The acylhalide compound may be selected from the group consisting of acetylchloride, pivaloylchloride and ethylchloroformate.

The amount of the acid, alkylsilylhalide compound or acylhalide compound is preferably in the range of about 0.1~10 eq., more preferably 0.5 ~5 eq., based on the amount of the compound of formula 3.

The solvent may be selected from the group consisting of 1,2-dichloroethane, ethylacetate, tetrahydrofuran, toluene, 1,4-dioxane, dimethylformamide, 2-methoxyethylether and a mixture thereof.

The reaction may be performed preferably in reflux. Accordingly, the reaction temperature in the process of the present invention is dependent on a solvent employed. The reaction may be completed preferably in about 1~48 hours, more preferably about 1~24 hours.

The present invention is further illustrated and described by the following examples, which should not be taken to limit the scope of the invention.

EXAMPLE 1

Synthesis of 1,2,3,9-tetrahydro-9-methyl-3-[(2-methyl-1H-imidazole-1-yl)methyl]-4H-carbazol-4-one 2.0 g of 1,2,3,9-tetrahydro-9-methyl-4H-carbazol-4-one, 1.65 g of 2-methyl imidazole and 2 ml of N,N,N',N'-tetramethyldiaminomethane were suspended in 30 ml of acetonitrile, and then 4 ml of chlorotrimethylsilane was slowly added thereto. The reaction mixture was stirred under reflux for 10 hours. The reaction mixture was concentrated to remove the solvent, and then 40 ml of water was added to the resulting residue. The resulting solid was filtered and dried, which was then suspended in acetone and stirred for 3 hours, and then filtered and dried under a reduced pressure to give 1.76 g of title compound (yield 60%).

EXAMPLE 2

Synthesis of 1,2,3,9-tetrahydro-9-methyl-3-[(2-methyl-1H-imidazole-1 -yl)methyl]-4H-carbazol-4-one 2.0 g of 1,2,3,9-tetrahydro-9-methyl-4H-carbazol-4-one, 1.65 g of 2-methyl imidazole and 2 ml of N,N,N',N'-tetramethyldiaminomethane were suspended in 20 ml of N,N-dimethylformamide, and then 4 ml of chlorotrimethylsilane was slowly added thereto. The reaction mixture was stirred at 90° C. for 10 hours. 100 ml of water was added to the reaction mixture. The resulting solid was filtered and dried, which was then suspended in acetone and stirred for 3 hours, and then filtered and dried under a reduced pressure to give 1.93 g of title compound (yield 66%).

EXAMPLE 3

Synthesis of 1,2,3,9-tetrahydro-9-methyl-3-[(2-methyl-1H-imidazole-1-yl)methyl]-4H-carbazol-4-one hydrochloride dihydrate 2.0 g of 1,2,3,9-tetrahydro-9-methyl-4H-carbazol-4-one, 1.65 g of 2-methyl imidazole and 2 ml of N,N,N',N'-tetramethyldiaminomethane were suspended in 5 ml of acetonitrile and 30 ml of toluene, and then 4 ml of chlorotrimethylsilane was slowly added thereto. The reaction mixture was stirred under reflux for 10 hours. The reaction mixture was concentrated to remove the solvent, and then 50 ml of water was added to the resulting residue. The resulting solid was filtered and dried, which was then suspended in acetone and stirred for 3 hours. The resulting solid was filtered and dried under a reduced pressure, which was then suspended in acetone, and then HCl was slowly added to thereto. The resulting suspension was stirred for 3 hours and cooled at 10° C. and below, which was then additionally stirred for 1 hour. The resulting solid was filtered and washed with acetone. The resulting solid was suspended in dichloromethane, which was then stirred under reflux for 1 hour and cooled at room temperature. The resulting solid was filtered and recrystallized with 10% aq. isopropyl alcohol to give 1.94 g of title compound (yield 53%).

EXAMPLE 4

Synthesis of 1,2,3,9-tetrahydro-9-methyl-3-[(2-methyl-1H-imidazole-1 -yl)methyl]-4H-carbazol-4-one 2.0 g of 1,2,3,9-tetrahydro-9-methyl-4H-carbazol-4-one, 1.65 g of 2-methyl imidazole and 2 ml of N,N,N',N'-tetramethyldiaminomethane were suspended in 30 ml of acetonitrile, and then 1.4 g of aluminum chloride was slowly added thereto. The reaction mixture was stirred under reflux for 10 hours. 150 ml dichloromethane and 50 ml of 1N aq. sodium hydroxide were added to the reaction mixture. The resulting organic layer was separated and dried over MgSO$_4$, and then evaporated. The resulting solid was suspended in acetone and stirred for 3 hours, and then filtered and dried under a reduced pressure to give 1.61 g of title compound (yield 55%).

EXAMPLE 5

Synthesis of 1,2,3,9-tetrahydro-9-methyl-3-[(2-methyl-1H-imidazole-1-yl)methyl]-4H-carbazol-4-one 2.0 g of 1,2,3,9-tetrahydro-9-methyl-4H-carbazol-4-one, 1.65 g of 2-methyl imidazole and 2.74 g of dipiperidinomethane were suspended in 20 ml of N,N-dimethylformamide, and then 4 ml of chlorotrimethylsilane was slowly added thereto. The reaction mixture was stirred for 8 hours at 90° C. 100 ml of water was added to the reaction mixture. The resulting solid was filtered and dried, which was then suspended in acetone and stirred for 3 hours, and then filtered and dried under a reduced pressure to give 1.99 g of title compound (yield 68%).

EXAMPLE 6

Synthesis of 1,2,3,9-tetrahydro-9-methyl-3-[(2-methyl-1H-imidazole-1-yl)methyl]-4H-carbazol-4-one 2.0 g of 1,2,3,9-tetrahydro-9-methyl-4H-carbazol-4-one, 1.65 g of 2-methyl imidazole and 274 g of dipiperidinomethane were suspended in 30 ml of acetonitrile, and then 2 g of aluminum chloride was slowly added thereto. The reaction mixture was stirred under reflux for 10 hours. 150 ml dichloromethane and 50 ml of 1N aq. sodium hydroxide were added to the reaction mixture. The resulting organic layer was separated and dried over $MgSO_4$, and then evaporated. The resulting solid was suspended in acetone and stirred for 3 hours, and then filtered and dried under a reduced pressure to give 2.05 g of title compound (yield 70%).

EXAMPLE 7

Synthesis of 1,2,3,9-tetrahydro-9-methyl-3-[(2-methyl-1H-imidazole-1 -yl)methyl]-4H-carbazol-4-one 2.0 g of 1,2,3,9-tetrahydro-9-methyl-4H-carbazol-4-one, 2 ml of N,N,N',N'-tetramethyl- diaminomethane were suspended in 30 ml of toluene, and then 1.4 ml of acetyl chloride was slowly added thereto, which was then stirred for 10 min. 1.65 g of 2-methyl imidazole was added to the reaction mixture, which was then stirred under reflux for 10 hours. The reaction mixture was concentrated to remove the solvent, and then 150 ml dichloromethane and 50 ml of 1 N aq. sodium hydroxide were added to the resulting residue. The resulting organic layer was separated and dried over $MgSO_4$, and then evaporated. The resulting solid was suspended in acetone, which was then stirred for 3 hours, and then filtered and dried to give 1.70 g of title compound (yield 58%).

EXAMPLE 8

Synthesis of 1,2,3,9-tetrahydro-9-methyl-3-[(2-methyl-1H-imidazole-1 -yl)methyl]-4H-carbazol-4-one At −10° C., 4 ml of N,N,N',N'-tetramethyldiaminomethane was slowly added to 46 ml of trifluoroacetic acid, which was then stirred for 30 min. 2.0 g of 1,2,3,9-tetrahydro-9-methyl-4H-carbazol-4-one and 8 g of 2-methyl imidazole was added to the reaction mixture, which was then stirred for about 8 hours at 120~130° C. After completion of reaction, the reaction mixture was cooled at room temperature, and then 1N aq. sodium hydroxide was added thereto. The resulting solid was filtered and washed with water, and then dried. The resulting solid was suspended in 80 ml of methanol, and then 0.28 g of active carbon was added thereto, which was then stirred under reflux for 1 hour. The resulting mixture was filtered and washed with methanol, and then evaporated to give 2.2 g of 1,2,3,9-tetrahydro-9-methyl-3-[(2-methyl-1H-imidazol-1-yl)methyl]-4H-carbazol-4-one (yield 75%).

EXAMPLE 9

Synthesis of 1,2,3,9-tetrahydro-9-methyl-3-[(2-methyl-1H-imidazole-1-yl)methyl]-4H-carbazol1-4-one To the solution of 7.1 ml of 1,3,5-trimethylhexahydro-1,3,5-triazine in 150 ml of toluene, was slowly added 4 ml of trifluoroacetic acid, which was then stirred for 10 min. 10 g of 1,2,3,9-tetrahydro-9-methyl-4H-carbazol-4-one and 20 g of 2-methyl imidazole were subsequently added to the reaction mixture, which was then stirred under reflux. After completion of reaction, the reaction mixture was evaporated, and then 200 ml of water was added to the resulting residue, which was then stirred for 2 hours at room temperature. The resulting solid was filtered and washed with excess water to give 7.5 g of light yellow title compound (yield 51%).

EXAMPLE 10

Synthesis of 1,2,3,9-tetrahydro-9-methyl-3-[(2-methyl-1H-imidazole-1 -yl)methyl]-4H-carbazol-4-one To the solution 19.5 g of 1,3,5-trimethylhexahydro-1,3,5-triazine in 20 ml of actonitrile and 150 ml of toluene, was slowly added 19 ml of chlorotrimethylsilane, which was then stirred for 10 min. 10 g of 1,2,3,9-tetrahydro-9-methyl-4H-carbazol-4-one and 8.2 g of 2-methyl imidazole was subsequently added to the reaction mixture, which was then stirred under reflux. After completion of reaction, the reaction mixture was evaporated, and then 200 ml of water was added to the resulting residue, which was then stirred for 2 hours at room temperature. The resulting solid was filtered and washed with water to give 7.95 g of light yellow title compound (yield 54%).

EXAMPLE 11

Synthesis of 1,2,3,9-tetrahydro-9-methyl-3-[(2-methyl-1H-imidazole-1 -yl)methyl]-4H-carbazol-4-one To the solution of 36 ml of acetyl chloride in 50 ml of actonitrile and 750 ml of toluene, was slowly added 51 ml of N,N,N',N'-tetramethyldiaminomethane at 0° C., which was then stirred for 10min. 50 g of 1,2,3,9-tetrahydro-9-methyl-4H-carbazol-4-one and 100 g of 2-methyl imidazole was subsequently added to the reaction mixture, which was then stirred under reflux. After completion of reaction, the reaction mixture was evaporated, and then 150 ml of water was added to the resulting residue. The resulting solid was filtered and washed, and then dried under a reduced pressure. The resulting solid was suspended in 350 ml of methanol, and then 0.7 g of active carbon was added to thereto, which was then stirred for 1 hour under reflux. The resulting mixture was filtered and washed with methanol, which was then stirred for 3 hours at room temperature. The resulting solid was filtered and dried to give 60 g of pure white title compound (yield 81.5%).

EXAMPLE 12

Synthesis of 1,2,3,9-tetrahydro-9-methyl-3-[(2-methyl-1H-imidazole-1-yl)methyl]-4H-carbazol-4-one hydrochloride dihydrate 29.4 g of 1,2,3,9-tetrahydro-9-methyl-3-[(2-methyl-1H-imidazol-1-yl)methyl]-4H- carbazol-4-one obtained in Example 9 was suspended in 300 ml of ethanol and 14 ml of water, which was then cooled at −10° C. 12.5 g of conc. HCl was slowly added to the reaction mixture, which was then stirred at room temperature for 2 hours. The resulting solid was filtered and washed with cold ethanol, and then dried in vacuous at 35° C. to give 32.6 g of title compound (yield 90%).

EXAMPLE 13

Synthesis of 1,2,3,9-tetrahydro-9-methyl-3-[(2-methyl-1H-imidazole-1-yl)methyl]-4H-carbazol-4-one hydrochloride dihydrate To the solution of 11 ml of acetyl chloride in 350 ml of actonitrile, was slowly added 21 ml of N,N,N',N'-tetramethyldiaminomethane at 0° C., which was then stirred for 10 min. 20 g of 1,2,3,9-tetrahydro-9-methyl-4H-carbazol-4-one and 50 g of 2-methyl imidazole was subsequently added to the reaction mixture under reflux. After completion of reaction, the resulting solid was filtered and washed with acetonitrile and water, and then dried. The resulting solid was suspended in 250 ml of ethanol, and 11 ml of conc. HCl was slowly added thereto, which was then stirred for 2 hours. The resulting solid was filtered and washed with cold ethanol, and then re-crystallized with water to give 28.3 g of pure white title compound (yield 78%).

As shown above, the present invention provides a process for preparing 1,2,3,9-tetrahydro-9-methyl-3-[(2-methyl-1H-imidazole-1 -yl)methyl]-4H-carbazol-4-one or its salt in high yield by one-step reaction, so as to be favorably applied to a large-scale mass production thereof.

What is claimed is:

1. A process for preparing a compound of formula 1, which comprises: allowing a compound of formula 2 to react with a compound of formula 3A or 3B and a compound of formula 4 in the presence of an acid, an alkylsilylhalide compound or an acylhalide compound, in a solvent:

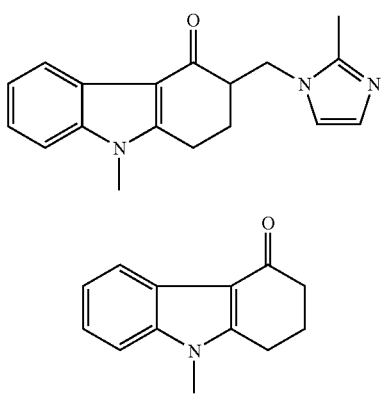

1

2

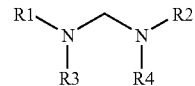

3A

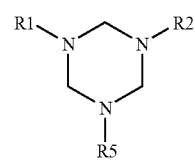

3B

4 wherein $R^1$, $R^2$, $R^3$ and $R^4$ are each independently $C_{1-6}$ alkyl or phenyl; or $R^1$ and $R^3$, and $R^2$ and $R^4$ are fused together with the nitrogen atoms to which they are attached to form a 6-membered heterocycloalkyl group optionally containing O; and $R^{1'}$, $R^{2'}$ and $R^5$ are each independently $C_{1-6}$ alkyl or aryl.

2. The process of claim 1, wherein the compounds of formulae 3A and 3B are each independently selected from the group consisting of N,N,N',N'-tetramethyldiaminomethane, N,N,N',N'-tetraethyldiaminomethane, N,N,N',N'-tetrabutvldiaminomethane, dipiperidinomethane, 4,4'-methylenedimorpholine, 1,3,5-triethylhexahydro, 1,3,5-triazine and 1,3,5-trimethylhexahydro-1,3,5-triazine.

3. The process of claim 1, wherein the compound of formula 3A or 3B is employed in an amount of 0.3 eq.~10 eq. to the compound of formula 2.

4. The process of claim 1, wherein the compound of formula 4 is employed in an amount of 1 eq.~10 eq. to the compound of formula 2.

5. The process of claim 1, wherein the acid is selected from the group consisting of hydrochloric acid, sulfuric acid, acetic acid, trifluoroacetic acid, methanesulfonic acid, aluminum chloride, zinc chloride, iron chloride(III), iron chloride(II), tin chloride and boron trifluoride.

6. The process of claim 1, wherein the alkylsilylhalide compound is selected from the group consisting of chlorotrimethylsilane, trichloromethylsilane and t-butyldimethylsilyl chloride.

7. The process of claim 1, wherein the acylhalide compound is selected from the group consisting of acetylchloride, pivaloylchloride and ethylchloroformate.

8. The process of claim 1, wherein the acid, alkylsilylhalide compound or acylhalide compound is employed in an amount of 0.1 eq.~10 eq. to the compound of formula 3A or 3B.

9. The process of claim 1, wherein the solvent is selected from the group consiting of 1,2-dichloroethane, ethylacetate, tetrahydrofuran, toluene, 1,4-dioxane, dimethylfonnamide, 2-methoxyethylether and a mixture thereof.

10. The process of claim 1, wherein the reaction is performed in reflux.

* * * * *